United States Patent [19]

Cohen et al.

[11] Patent Number: 5,034,433
[45] Date of Patent: Jul. 23, 1991

[54] COMPOSITE DENTAL CEMENT COMPOSITION CONTAINING TITANIUM

[75] Inventors: Brett I. Cohen, Nanuet; Allan S. Deutsch, New York, both of N.Y.; Brahma D. Sharma, Louisville, Colo.

[73] Assignee: Essential Dental Systems, Inc., South Hackensack, N.J.

[21] Appl. No.: 508,095

[22] Filed: Apr. 10, 1990

[51] Int. Cl.5 .......................... A61K 6/08; C08J 3/12; C08K 3/40; C08L 63/00
[52] U.S. Cl. .................. 523/400; 523/109; 523/116; 523/118; 523/120
[58] Field of Search ............... 523/109, 116, 118, 120, 523/400

[56] References Cited

U.S. PATENT DOCUMENTS

| | | | |
|---|---|---|---|
| 3,066,112 | 11/1962 | Bowen | 523/116 |
| 3,539,533 | 11/1970 | Lee, II | 524/560 |
| 3,801,344 | 4/1974 | Dietz | 106/300 |
| 3,808,170 | 4/1974 | Rogers | 523/117 |
| 3,882,600 | 5/1975 | Plymale | 32/15 |
| 3,926,906 | 12/1975 | Lee et al. | 523/116 |
| 3,991,008 | 11/1976 | Temin et al. | 523/116 |
| 3,997,504 | 12/1976 | Plymale | 523/116 |
| 4,051,598 | 10/1977 | Sneer | 32/10 A |
| 4,107,845 | 8/1978 | Lee, Jr. et al. | 32/15 |
| 4,117,595 | 10/1978 | Ibsen et al. | 32/8 |
| 4,141,144 | 2/1979 | Lustgarten | 32/15 |
| 4,150,012 | 4/1979 | Joos | 523/116 |
| 4,188,317 | 2/1980 | Temin | 524/443 |
| 4,197,234 | 4/1980 | Temin | 523/116 |
| 4,261,879 | 4/1981 | Kemper | 523/118 |
| 4,327,014 | 4/1982 | Kawahara et al. | 523/116 |
| 4,347,174 | 8/1982 | Nagase et al. | 523/116 |
| 4,383,826 | 5/1983 | Butler et al. | 433/228 |
| 4,386,912 | 6/1983 | Nagase et al. | 433/228 |
| 4,407,984 | 10/1983 | Ratcliffe et al. | 523/115 |
| 4,431,421 | 2/1984 | Kawahara et al. | 433/228 |
| 4,437,836 | 3/1984 | Schmitz-Josten et al. | 433/199 |
| 4,440,878 | 4/1984 | Kawahara et al. | 523/116 |
| 4,449,938 | 5/1984 | Pollak | 523/116 |
| 4,454,258 | 7/1984 | Kawahara et al. | 523/116 |
| 4,542,539 | 9/1985 | Rowe, Jr. et al. | 623/16 |
| 4,552,906 | 11/1985 | Podszin et al. | 523/115 |
| 4,610,631 | 9/1986 | Beyer et al. | 433/228 |
| 4,648,845 | 3/1987 | Orlowski et al. | 433/217 |
| 4,695,251 | 9/1987 | Randklev | 433/8 |
| 4,772,325 | 9/1988 | Kwan et al. | 106/35 |
| 4,801,528 | 1/1989 | Bennett | 433/220 |
| 4,918,136 | 4/1990 | Kawaguchi et al. | 523/116 |

*Primary Examiner*—John Kight, III
*Assistant Examiner*—Kathryne J. Shelbourne
*Attorney, Agent, or Firm*—Gottlieb, Rackman & Reisman

[57] ABSTRACT

A composite dental cement composition that is suitable for application with dental posts for either post insertion in a tooth or during core formation is provided. The cement composition includes a polymer matrix in an amount between about 15 and 50 weight percent, a filler in an amount between about 35 and 80 weight percent, and titanium in an amount between about 1 and 15 weight percent. The titanium ingredient chemically interacts with the polymer matrix in order to increase compressive strength of the cement composition. A fluoride compound may be added in order to substantially eliminate caries and further tooth decay.

30 Claims, No Drawings

COMPOSITE DENTAL CEMENT COMPOSITION CONTAINING TITANIUM

BACKGROUND OF INVENTION

This invention relates to a restorative composite dental cement composition, and more particularly, to a dental cement composition having a substantially high compressive strength that is suitable for application with a dental post or as a core build-up material.

Dental restorative cement compositions have achieved wide commercial success and are extensively used in clinical dental practice. The leading U.S. patent on dental restorative cement compositions is U.S. Pat. No. 3,066,112 to Bowen, which describes a dental cement composition that consists of a liquid polymerizable organic resin matrix and finely divided inorganic filler materials.

As described in the Bowen patent, the liquid polymerizable organic resin matrix is typically prepared by combining bisphenol A-glycidyl methacrylate with one or more active monomers, preferably other methacrylates. As part of the system, a catalyst or initiator is used, such as benzoyl peroxide, along with a base or polymerization accelerator such as a toluidine compound. Other ingredients such as stabilizers, absorbents and pigments may be added to the composition.

Although the compositions described in the Bowen patent, as well as those described in subsequent patents and references, are somewhat satisfactory, a major disadvantage of most prior art composite dental cement compositions is that they have a compressive strength when applied which is far from adequate. The compressive strength of a restorative composite dental cement composition is important for enhancing the wearability of the restorative composition.

Accordingly, it would be desirable to provide a restorative composite dental cement composition having a high compressive strength whose viscosity may be varied depending upon the desired dental application.

SUMMARY

Generally speaking, in accordance with the invention, a composite dental cement composition containing titanium is provided. The composite dental cement composition includes a polymer matrix in an amount of between about 15 and 50 weight percent, a filler in an amount of between about 35 and 80 weight percent and titanium in an amount between about 1 and 15 weight percent. The composite dental cement composition is suitable for use in connection with dental post insertion into a post-hole formed in a tooth after a root canal procedure. The cement composition may also be used in connection with core buildup after dental post affixation in the tooth.

The composite dental cement composition of the invention is prepared by combining a catalyst component and a base component. The catalyst component includes a catalyst, a least one epoxy monomer and a filler. In application, the catalyst and base components are combined, which causes a setting reaction to take place.

In preparing the inventive composite composition, titanium is added either to the catalyst component, base component, or both prior to combining the base and catalyst components. The addition of titanium substantially increases the compressive strength of the composition.

Accordingly, it is an object of this invention to provide an improved composite dental cement composition which is suitable for application with a dental post.

Yet another object of the invention is to provide an improved dental cement composition which includes titanium for increasing compressive strength and overall wear of the composition.

Another object of the invention is to provide an improved composite dental cement composition which may either have a low viscosity or a high viscosity depending upon the desired application.

Yet a further object of the invention is provide an improved composite dental cement composition which is prepared by combining a catalyst component and a base component.

It is still another object of the invention to provide an improved composite dental cement composition in which the epoxy monomer of the catalyst component and the epoxy monomer of the base component undergo extensive polymerization.

A further object of the invention is to provide an improved composite dental cement composition which includes a fluoride compound to substantially eliminate root caries and further tooth decay.

Still other objects and advantages of the invention will in part be obvious and will in part be apparent from the following description.

The invention accordingly comprises the several steps and the relation of one or more of the steps with respect to each of the others, and the composition or compositions having the features, properties, and a relation of constituents which are exemplified in the following detailed disclosure, and the scope of the invention will be indicated in the claims.

DETAILED DESCRIPTION OF THE PREFERRED EMBODIMENTS

The composite dental cement composition of the invention includes a polymer matrix in an amount between about 15 and 50 weight percent. Preferably, the polymer matrix comprises an epoxy matrix, and even more preferably an acrylic matrix. The acrylic matrix is formed from monomers of acrylates and methacrylates, such as di-, tri- and tetra-acrylates and methacrylates.

Suitable monomers of diacrylates include ethylene glycol diacrylate, diethylene glycol diacrylate, 1,4-dimethylolcyclohexane diacrylate and $C_2$-$C_{12}$ alkylene diacrylates.

Suitable monomers of dimethacrylate include bisphenol A-glycidyl methacrylate (BIS-GMA), triethylene glycol dimethacrylate, tetraethylene glycol dimethacrylate, ethylene glycol dimethacrylate, diethylene glycol dimethacrylate, butanediol dimethacrylate, hexanediolethylene dimethacrylate, neopentyl glycol dimethacrylate, isobisphenol A-glycidyl methacrylate, trimethylolpropane dimethylacrylate, bisphenol A-ethoxylated dimethacrylate and bisphenol A-dimethacrylate. The preferred monomer of dimethacrylate is bisphenol A-glycidylmethacrylate (BIS-GMA) and is present in an amount between about 5 and 50 weight percent based on the total weight of the cement composition.

Suitable monomers of triacrylates and trimethacrylates include trimethylolpropane triacrylate, tetramethylmethane triacrylate, tetramethylolmethane trimethylacrylate, trimethylolethane trimethacrylate and trimethylolpropane trimethacrylate.

Suitable monomers of tetracrylates and tetramethacrylates include tetramethyolmethane tetraacrylate and tetramethylol methane tetramethacrylate.

The purpose of the polymer matrix, specifically the acrylic matrix formed from monomers of acrylates and methacrylates, is to provide a binding network for the filler to be incorporated, thereby providing strength to the composite cement composition.

The filler of the inventive composite cement composition is selected from the group including quartz, silicon dioxide, fumed silicon dioxide, aluminum dioxide, titanium dioxide, zirconium dioxide, silicas, glass, graphite fibers, boron fibers, barium glass, alumino silicates, boro silicate glass, glass powders, hydroxy apatite, wood, micas and asbestos. The function of the filler ingredient is to be incorporated with the polymer matrix for adding strength to the overall inventive composition.

The titanium component is present in the inventive composition in an amount between about 1 and 15 weight percent.

Preferably, at least some of the titanium component of the inventive composite dental cement is chemically treated, and more preferably silanated using a silane compound selected from the group including gamma-methacryloxy propyltri-methoxysilane (A-174), gamma-methacryloxy propyl-tris-(2-methoxyethoxy) silane (A-175), vinyl trichlorosilane, vinyl triethoxysilane, vinyl trimethoxysilane and vinyl triacetoxysilane.

In Example 1 found below, the silanation of titanium powder is described.

EXAMPLE 1

The 25.15 grams of titanium powder (black) was placed in a 50 ml screw cap vile. Then, 0.5 ml (0.51 gram) of gamma methacryloxy-propyltrimethoxysilane (A-174) was added by use of a syringe, after which the syringe was washed with 3 ml of cyclohexane. Then, 1.4 ml of N-propylamine (1.04 grams) was added to the mixture also by syringe followed by 3 ml of an additional amount of cyclohexane in order to form a blacklike suspension. The suspension was mixed for one and one half hours, after which the mixture was allowed to evaporate for approximately 24 hours. After 24 hours of evaporation, the remaining black powder was transferred to a 100 ml beaker where it was washed three times with 30 ml of cyclohexane. The purpose of the washing was to remove any soluble silane by-products and any residual N-propylamine. Thereafter, the resulting black powder was then allowed to air dry for an additional 24 hours after which 24.69 grams of a black powder was recovered (98% weight recovery). The resulting solid was found to be hydrophobic to water, illustrating that the titanium powder had been silanated.

As shown in Example 1, the preferred silane for chemically treating the titanium ingredient of the inventive composite dental cement composition is gamma-methacryloxypropyltrimethoxysilane (A-174).

The purpose of chemically treating the titanium ingredient is to chemically interact with the polymer matrix, thereby forming a copolymer-like titanium polymer matrix.

Although the inventive dental cement composite composition contains titanium in an amount between 1 and 15 weight percent, it is preferred that the titanium is present in an amount betWeen 2 and 5 weight percent based on the total weight of the composition. Also, it is preferred that the titanium used is titanium powder having a particle size of between about 1 and 30 microns and a purity of at least 98%.

Optionally, a fluoride compound may be added to the inventive composite dental cement composition in an amount between 0.5 and 6 weight percent. The purpose of the fluoride compound is to substantially eliminate root caries and further tooth decay. The fluoride compound is chosen from the group including sodium fluoride, tin fluoride, ytterbium fluoride, fluoride chosen from amine fluorides and fluorides chosen from aciduated phosphate fluorides.

In order to prepare the composite dental cement of the composition, a catalyst component and a base component are mixed together, which causes a chemical setting reaction. Particularly, the catalyst component includes a catalyst or polymerization initiator in an amount between about 0 2 and 2.0 weight percent, at least one epoxy monomer in an amount between 15 and 50 weight percent and a filler in an amount between about 40 and 80 weight percent.

The catalyst of the catalyst component is typically a free radical source, and more preferably an organic peroxide. Suitable organic peroxides include benzoyl peroxide, acetyl peroxide, parachlorobenzoyl peroxide, cumyl peroxide, t-butyl peroxide, lauroyl peroxide, t-butyl hydroperoxide, methylethyl-ketone peroxides, t-butyl peroxybenzoate, 2,5 dimetylhexane-2,5 dihydroperoxide and t-cumyl hydroperoxide. Benzoyl peroxide is the most preferred catalyst for the catalyst component.

The base component which is used for preparing the composite dental cement composition includes a base or accelerator in an amount between about 0.2 and 1.5 weight percent, at least one epoxy monomer in an amount between about 20 and 50 weight percent and a filler in an amount between about 45 and 85 weight percent. Preferably, the base of the base component is an amine compound chosen from amines such as propylamine, N-butylamine, pentylamine, hexylamine, dimethylamine, diethylamine, dipropylamine, di-n-butylamine, dipentylamine, trimethylamine, triethylamine, tripropylamine, tri-n-butylamine, tripentylamine, 4-methylaniline, N-N-bis-(2-hydroxyethyl)-3,5-dimethylaniline, N-methyl-N (2-hydroxyethyl)-4-methylaniline and long chain fatty amines such as NN' dimethylaniline and N-methyldiphenylamine. Diamines can also be used such as ethylene diamine, trimethylene diamine, tetramethylene diamine, pentamethylene diamine and hexamethylene diamine.

As will be shown in the examples hereinbelow, the preferred amine is NN' dihydroxyethyl toluidine. Other toluidines may be used such as N,N-dimethyl-p-toluidine and N,N-diethyl-p-toluidine.

For either the catalyst or base components, the epoxy monomer is chosen preferably from monomers of methacrylate, as described hereinabove.

When the catalyst and base components are combined, a chemical setting reaction takes place which will last on the average of three to five minutes in order to fully set the inventive composite dental cement composition.

When combining the catalyst and base components, titanium (either chemically modified or not) is added. The titanium ingredient may be added either to the catalyst or base component, or to both, prior to combining the two components. Alternatively, the titanium ingredient may be added to the base and catalyst components immediately after they are combined. Preferably, the chemically treated or modified titanium ingredient should be added to either the base, catalyst or both, prior to combining the two components. This insures the proper wetting of the chemically treated (e.g. silinated) titanium compound.

Preferably, substantially equal amounts of catalyst component and base component are combined in order to form the inventive composite dental cement composition. Once the catalyst and base components are combined, the peroxide compound contained in the catalyst component is fully initiated when brought into contact with the amine compound (free radicals are formed) found in the base component. As a result, substantial polymerization of the acrylic monomers takes place, resulting in a strong polymer matrix of the inventive composite dental cement composition.

Titanium is added to the inventive composite dental cement composition in order to interact with the polymer matrix (to form a copolymer-like composition) for increasing compressive strength of the resulting composition, and for increasing wear of the overall inventive composition. Additionally, reduction of the coefficient of thermal expansion may be associated with the inventive composition. Other ingredients, such as stabilizers and absorbents, may be present to increase shelf life and prevent degradation of properties. Also, various dyes or pigments may be added to obtain various color shades for conforming to the tooth color to which the inventive composition is applied.

In order to better comprehend the inventive composite dental cement composition, the following examples are provided. In each example, a substantially equal amount of the base and catalyst components were mixed for approximately 30 seconds in order to initiate a chemical setting reaction, resulting in formation of the composite dental cement composition.

EXAMPLE 2 (CONTROL)

| Catalyst Formulation | |
|---|---|
| 5u quartz silanized | 57.185 weight percent (57.185 grams) |
| BIS-GMA | 26.9745 weight percent (26.9745 grams) |
| Triethylene glycol dimethacrylate with BHT | 10.601 weight percent (10.601 grams) |
| Aluminium oxide C | 2.4586 weight percent (2.4586 grams) |
| Cabosil M-5 | 1.2293 weight percent (1.2293 grams) |
| Benzoyl peroxide | 0.9017 weight percent (0.9017 gram) |
| Aerosil R-972 | 0.6147 weight percent (0.6147 gram) |
| BHT | 0.03514 weight percent (0.03514 gram) |
| Base Formulation | |
| Ground kimble glass silanized | 35.808 weight percent (35.808 grams) |
| 5u quartz silanized | 23.625 weight percent (23.625 grams) |
| BIS-GMA | 18.144 weight percent (18.144 grams) |
| Ethoxylated bisphenol A-dimethacrylate with BHT | 12.096 weight percent (12.096 grams) |
| 1,6 hexamethylene dimethacrylate | 5.040 weight percent (5.040 grams) |
| Triethylene glycol dimethacrylate with MEHQ | 4.0915 weight percent (4.0915 grams) |

| -continued | |
|---|---|
| NN' dihydroxyethyl-p-toluidine | 0.4900 weight percent (0.49000 gram) |
| Uvinul 400 | 0.3578 weight percent (0.3578 gram) |
| Bisphenol A-dimethacrylate | 0.1008 weight percent (0.1008 gram) |
| Titanium dioxide | 0.006 weight percent (0.006 gram) |
| Tint concentrate | 0.002057 weight percent (0.002057 gram) |

In order to prepare the catalyst components, 10.601 grams of triethylene glycol dimethacrylate with BHT (butylated hydroxytoluene), 0.03514 gram of BHT and 0.9017 gram of benzoyl peroxide were mixed until the BHT and benzoyl peroxide reagants were fully dissolved in the triethylene glycol dimethaerylate. Then, warm BIS-GMA (26.9745 grams) was added to the above mixture and stirred until the resulting mixture was a homogenous solution. Then, aerosil R-972 (0.6147 gram), cabosil M-5 (1.2293 grams) (amorphous fumed silica), aluminium oxide C (2.4586 grams) and 5u quartz silanized (57.185 grams) were blended together (mixed for 10 mins) and then added to the resulting resin mixture. This resulted in approximately 100 grams of the catalyst component portion of the composition.

In order to prepare the base component, 5.040 grams of 1,6 hexamethylene dimethacrylate, 4.0915 grams of triethylene glycol dimethacrylate with MEHQ (4-methoxyphenol), 0.3578 grams of uvinul 400 (2,4 dihydroxy benzophenone), 0.1008 grams of bisphenol A-dimethacrylate, and 0.4900 grams of NN'dihydroxyethyl-p-toluidine were all mixed together until a homogenous solution resulted. Then, 12.096 grams of ethyoxylated bisphenol A-dimethacrylate with BHT in warm BIS-GMA (16.144 grams) were added to the above solution until a second homogenous solution resulted. Then, tint concentrate (0.002057 grams), titanium dioxide (0.006 grams), aerosil R-972 (0.2387 grams), 5u quartz silanized (23.625 grams), and ground kimble glass silanized (35.808 grams) were all mixed together to give a white powder mixture. This white powder mixture was then mixed with the BIS-GMA resin solution that was mixed before and approximately 100 grams of the base portion of the composition was obtained.

Then, equal weights of the base and catalyst (5 grams/5 grams) components were mixed for 30 seconds. This mixing produced a setting reaction which lasted for about 3-5 minutes. As a result, a composite dental cement is formed having a compressive strength after placed for 24 hours in water of 29534 psi.

EXAMPLE 3

Equal amounts of the base component (5 grams) and the catalyst component (5 grams) described in Example 2 were mixed. Immediately thereafter, a non-chemically treated titanium powder (0.2040 gram) was added to the mixture of base and catalyst components and mixed for 30 seconds, producing a light grey material. This mixing caused a setting reaction which lasted for about 3-5 minutes. As a result, a composite dental cement was formed having a compressive strength after placed for 24 hours in water of 34534 psi.

EXAMPLE 4

Equal amounts of the base component (5 grams) and the catalyst component (5 grams) described in Example 2 were mixed. Immediately thereafter, chemically treated titanium powder (0.2040 gram) was added to the mixture of base and catalyst components and mixed for thirty seconds, producing a light grey material. This mixing caused a setting reaction which lasted for about 3-5 minutes. As a result, a composite dental cement was formed having a compressive strength after placed for 24 hours in water of 40048 psi.

EXAMPLE 5

Equal amounts of the base component (5 grams) and the catalyst components (5 grams) described in Example 2 were mixed. Immediately thereafter, chemically treated titanium powder (0.2040 gram) and a non-chemically treated titanium powder (0.102 gram) were added to the mixture of base and catalyst components and mixed for 30 seconds, producing a light grey material. This mixing caused a setting reaction to take place which lasted for about 3-5 minutes. As a result, a composite dental cement composition was formed having a compressive strength after placed for 24 hours in water of 41875 psi.

EXAMPLE 6

Equal amounts of the base component (5 grams) and the catalyst component (5 grams) described in Example 2 were mixed. Immediately thereafter, chemically treated titanium powder (0.2040 gram), non-chemically treated titanium powder (0.051 gram) and ytterbium fluoride (0.051 gram) were added to the mixture of base and catalyst components and mixed for 30 seconds, producing a light grey material. This mixing caused a setting reaction to take place which lasted for about 3-5 minutes. As a result, a composite dental cement was formed having a compressive strength after placed for 24 hours in water of 38064 psi.

EXAMPLE 7

Equal amounts of the base component (5 grams) and the catalyst component (5 grams) described in Example 2 were mixed. Immediately thereafter, chemically treated titanium powder (0.208 gram), non-chemically treated titanium powder (0.104 gram) and ytterbium fluoride (0.104 gram) were added to the mixture of base and catalyst components and mixed for 30 seconds, producing a light grey material. This mixing caused a setting reaction which lasted for about 3-5 minutes. As a result, a composite dental cement composition was formed having a compressive strength after placed for 24 hours in water of 37314 psi.

EXAMPLE 8 (CONTROL)

| Catalyst Formulation | |
| --- | --- |
| 5u quartz silanized | 57.185 weight percent (57.185 grams) |
| BIS-GMA | 26.9745 weight percent (26.9745 grams) |
| Triethylene glycol dimethacrylate with BHT | 10.601 weight percent (10.601 grams) |
| Aluminium oxide C | 2.4586 weight percent (2.4586 grams) |
| Cabosil M-5 | 1.2293 weight percent (1.2293 grams) |
| Benzoyl peroxide | 0.9017 weight percent (0.9017 gram) |
| Aerosil R-972 | 0.6147 weight percent (0.6147 gram) |
| BHT | 0.03514 weight percent (0.03514 gram) |
| Base Formulation | |
| Ground kimble glass silanized | 35.355 weight percent (35.808 grams) |
| 5u quartz silanized | 23.326 weight percent (23.625 grams) |
| BIS-GMA | 17.916 weight percent (18.144 grams) |
| Ethoxylated bisphenol A-dimethacrylate with BHT | 11.943 weight percent (12.096 grams) |
| 1,6 hexamethylene dimethacrylate | 4.9769 weight percent (5.040 grams) |
| Triethylene glycol dimethacrylate with MEHQ | 4.0397 weight percent (4.0915 grams) |
| NN' dihydroxyethyl-p-toluidine | 0.48379 weight percent (0.4900 gram) |
| Uvinul 400 | 0.35327 weight percent (0.3570 gram) |
| Aerosil R-972 | 0.23567 weight percent (0.2387 gram) |
| Bisphenol A-dimethacrylate | 0.09952 weight percent (0.1006 gram) |
| Titanium dioxide | 0.005924 weight percent (0.006 gram) |
| Tint concentrate | 0.0020309 weight percent (0.002057 gram) |
| Sodium fluoride | 1.2637 weight percent (1.28 grams) |

In order to prepare the catalyst component, 10.601 grams of triethylene glycol dimethacrylate with BHT, 0.03514 gram of BHT and 0.9017 gram of benzoyl peroxide were mixed until the BHT and benzoyl peroxide reagents were fully dissolved in the triethylene glycol dimethacrylate. Then, warm BIS-GMA (26.9745 grams) was added to the above powder mixture and stirred until the resulting mixture was a homogenous solution. Then, aerosil R-972 (0.6147 gram), cabosil M-5 (1.2293 grams), aluminium oxide C (2.4586 grams) and 5u quartz silanized (57.185 grams) were blended together (mixed for 10 minutes) and then added to the resulting resin mixture. This resulted in approximately 100 grams of the catalyst component of composition.

In order to prepare the base component, 5.040 grams of 1.6 hexamethylene dimethacrylate, 4.0915 grams of triethylene glycol dimethacrylate with MEHQ, 0.3578 grams of uvinul 400, 0.1006 grams of bisphenol A-dimethacrylate, and 0.4900 grams of NN'dihydroxyethl-p-toluidine were all mixed together until a homogenous solution resulted. Then 12.096 grams of ethyoxylated bisphenol A-dimethacrylate with BHT in warm BIS-GMA (18.144 grams) were added to the above solution until a second homogenous solution resulted. Then, tint concentrate (0.002057 grams), titanium dioxide (0.006 grams), aerosil R-972 (0.2387 grams), sodium fluoride (1.28 grams), 5u quartz silanized (23.625 gram), and ground kimble glass silanized (35.808 grams) were all mixed together to give a white powder mixture. This white powder mixture was then mixed with the BIS-GMA resin solution that was mixed before and approximately 101 grams of the base portion of the composition was obtained.

Then, equal weights of the base and catalyst (5 grams/5 grams) components were mixed for 30 seconds. This caused a setting reaction to take place which lasted for about 3-5 minutes. As a result, a composite dental cement was formed having a compressive strength after placed for 24 hours in water of 29400 psi.

EXAMPLE 9

Equal amounts of the base component (5 grams) and the catalyst component (5 grams) described in Example 8 were mixed. Immediately thereafter, chemically treated titanium powder (0.3646 gram) and non-chemically treated titanium powder (0.05200 gram) were added to the mixture of base and catalyst components and mixed for about 30 seconds, producing a light gray material. This mixing caused a setting reaction to take place which lasted for about 3-5 minutes. As a result, a composite dental cement was formed having a compressive strength after placed for 24 hours in water of 36332 psi.

EXAMPLE 10 (CONTROL)

| Catalyst Formulation | |
| --- | --- |
| 5u quartz silanized | 57.185 weight percent (57.185 grams) |
| BIS-GMA | 26.9745 weight percent (26.9745 grams) |
| Triethylene glycol dimethacrylate with BHT | 10.601 weight percent (10.601 grams) |
| Aluminium oxide C | 2.4586 weight percent (2.4586 grams) |
| Cabosil M-5 | 1.2293 weight percent (1.2293 grams) |
| Benzoyl peroxide | 0.9017 weight percent (0.9017 gram) |
| Aerosil R-972 | 0.6147 weight percent (0.6147 gram) |
| BHT | 0.03514 weight percent (0.03514 gram) |
| Base Formulation | |
| Ground kimble glass silanized | 35.0887 weight percent (35.808 grams) |
| 5u quartz silanized | 23.1504 weight percent (23.625 grams) |
| BIS-GMA | 17.7795 weight percent (18.144 grams) |
| Ethoxylated bisphenol A-dimethacrylate with BHT | 11.8530 weight percent (12.096 grams) |
| 1,6 hexamethylene dimethacrylate | 4.9387 weight percent (5.040 grams) |
| Triethylene glycol dimethacrylate with MEHQ | 4.0093 weight percent (4.0915 grams) |
| NN' dihydroxyethyl-p-toluidine | 0.48015 weight percent (0.4900 gram) |
| Uvinul 400 | 0.35061 weight percent (0.3578 gram) |
| Aerosil R-972 | 0.23390 weight percent (0.2387 gram) |
| Bisphenol A-dimethacrylate | 0.098775 weight percent (0.1008 gram) |
| Titanium dioxide | 0.005879 weight percent (0.006 gram) |
| Tint concentrate | 0.0020156 weight percent (0.002057 gram) |
| Sodium fluoride | 2.0088 weight percent (2.05 grams) |

In order to prepare the catalyst component, 10.601 grams of triethylene glycol dimethacrylate with BHT, 0.03514 gram of BHT and 0.9017 gram of benzoyl peroxide were mixed until the BHT and benzoyl peroxide reagents were fully dissolved in the triethylene glycol dimethacrylate. Then, warm BIS-GMA (26.9745 grams) was added to the above powder mixture and stirred until the resulting mixture was a homogenous solution. Then, aerosil R-972 (0.6147 gram), cabosil M-5 (1.2293 grams), aluminium oxide C (2.4586 grams) and 5u quartz silanized (57.185 grams) were blended together (mixed for 10 minutes) and then added to the resulting BIS-GMA resin mixture. This resulted in approximately 100 grams of the catalyst component of the composite.

In order to prepare the base component, 5.040 grams of 1,6 hexamethylene dimethacrylate, 4.0915 grams of triethylene glycol dimethacrylate with MEHQ, 0.3578 grams of uvinul 400, 0.1008 grams of bisphenol A-dimethacrylate, and 0.4900 grams of NN' dihydroxyethyl-p-toluidine were all mixed together until a homogenous solution resulted. Then, 12.096 grams of ethyoxylated bisphenol A-dimethacrylate with BHT in warm BIS-GMA (18.144 grams) were added to the above solution until a second homogenous solution resulted. Then, tint concentrate (0.002057 grams), titanium dioxide (0.006 grams), aerosil R-972 (0.2387 grams), sodium fluoride (2.05 grams), 5u quartz silanized (23.625 grams), and ground kimble glass silanized (35.808 grams) were all mixed together to give a white powder mixture. This white powder mixture was then mixed with the BIS-GMA resin solution that was mixed before and approximately 102 grams of the base component of the composite was obtained.

Then, equal weights of the base and catalyst (5 grams/5 grams) components were mixed for 30 seconds. This mixing caused a setting reaction to take place which lasted about 3-5 minutes. As a result, a composite dental cement was formed having a compressive strength after placed for 24 hours in water of 33400 psi.

EXAMPLE 11

Equal amounts of the base component (5 grams) and the catalyst component (5 grams) described in Example 10 were mixed. Immediately thereafter, chemically treated titanium powder (0.1894 gram) and a non-chemically treated titanium powder (0.05120 gram) were added to the mixture of base and catalyst components and mixed for 30 seconds, producing a light gray material. This mixing caused a setting reaction to take place which lasted for about 3-5 minutes. As a result, a composite dental cement was formed having a compressive strength after placed for 24 hours in water of 40829 psi.

EXAMPLE 12

Equal amounts of the base component (5 grams) and the catalyst component (5 grams) described in Example 10 were mixed. Immediately thereafter, chemically treated titanium powder (0.20408 gram) was added to the mixture of base and catalyst components and mixed for 30 seconds, producing a light gray material. This mixing caused a setting reaction which lasted for about 3-5 minutes. As a result, a composite dental cement was formed having a compressive strength after placed for 24 hours in water of 38139 psi.

EXAMPLE 13 (CONTROL)

| Catalyst Formulation | |
| --- | --- |
| 5u quartz silanized | 8.18 weight percent (8.18 grams) |
| 325 m quartz silanized | 66.43 weight percent (66.43 grams) |
| BIS-GMA | 5.11 weight percent (5.11 grams) |
| Triethylene glycol | 16.6 weight percent |

-continued

| | |
|---|---|
| dimethacrylate with MEHQ | (16.6 grams) |
| Aluminium oxide C | 3.066 weight percent (3.066 grams) |
| Benzoyl peroxide | 0.5826 weight percent (0.5826 gram) |
| BHT | 0.0254 weight percent (0.0254 gram) |
| Base Formulation | |
| 325 m quartz silanized | 53.1 weight percent (53.1 grams) |
| 5u quartz silanized | 16.65 weight percent (16.65 grams) |
| BIS-GMA | 13.03 weight percent (13.03 grams) |
| Ethoxylated bisphenol A-dimethacrylate | 8.69 weight percent (8.69 grams) |
| 1,6 hexamethylene dimethacrylate with MEHQ | 3.618 weight percent (3.618 grams) |
| Triethylene glycol dimethacrylate with MEHQ | 2.898 weight percent (2.896 grams) |
| NN' dihydroxyethyl-p-toluidine | 0.3618 weight percent (0.3618 gram) |
| Uvinul 400 | 0.261 weight percent (0.261 gram) |
| Titanium dioxide | 0.778 weight percent (0.778 gram) |
| Cabosil M-5 | 0.605 weight percent (0.605 gram) |
| MEHQ | 0.00534 weight percent (0.00534 gram) |

In order to prepare the catalyst component, 16.6 grams of triethylene glycol dimethacrylate with MEHQ, 0.0254 gram of BHT and 0.5826 gram of benzoyl peroxide were added together until the BHT and benzoyl peroxide reagents were fully dissolved in the triethylene glycol dimetharylate. Then, warm BIS-GMA (5.11 grams) was added and stirred to give a homogenous mixture. Then, a blended mixture of the following powders: aluminium oxide C (3.066 grams), 5u quartz silanized (8.18 grams) and 325 m quartz silanized powder (66.43 grams) was added to the resin mixture. This resulted in approximately 100 grams of the catalyst component of the composition.

In order to prepare the base component, 1,6 hexamethylene dimethacrylate with MEHQ (3.618 grams), triethylene glycol dimethacrylate with MEHQ (2.898 grams), MEHQ (0.00534 gram), uvinul 400 (0.261 gram), and NN' dihydroxyethyl-p-toluidine (0.3618 gram) were all mixed together to form a homogenous solution. Then, ethoxylated bisphenol A-dimethacrylate (8.69 grams) was added to produce a second homogenous solution after complete mixing. Then, warm BIS-GMA resin (13.03 grams) was added and stirred until a homogenous mixture also developed. Then, the following solids were blended together: titanium dioxide (0.778 gram), cabosil M-5 (0.605 gram), 5u quartz silanized (16.65 grams) and 325 m quartz silanized (53.1 grams). This blended mixture of powders was added to the BIS-GMA resin mixture prepared before to yield approximately 100 grams of the base component of the composition.

Then, equal amounts of the base and catalyst (5 grams/5 grams) components were mixed for 30 seconds. This mixing produced a setting reaction which lasted for about 3-5 minutes. As a result, a composite dental cement was formed having a compressive strength after placed for 24 hours in water of 33500 psi.

EXAMPLE 14

| | |
|---|---|
| Catalyst Formulation | |
| 5u quartz silanized | 8.18 weight percent (8.18 grams) |
| 325 m quartz silanized | 66.43 weight percent (66.43 grams) |
| BIS-GMA | 5.11 weight percent (5.11 grams) |
| Triethylene glycol dimethacrylate with MEHQ | 16.6 weight percent (16.6 grams) |
| Aluminium oxide C | 3.066 weight percent (3.066 grams) |
| Benzoyl peroxide | 0.5826 weight percent (0.5826 gram) |
| BHT | 0.0254 weight percent (0.0254 gram) |
| Base Formulation | |
| 325 m quartz silanized | 50.961 weight percent (53.1 grams) |
| 5u quartz silanized | 15.979 weight percent (16.65 grams) |
| BIS-GMA | 12.5051 weight percent (13.03 grams) |
| Ethoxylated bisphenol A-dimethacrylate | 0.3399 weight percent (8.69 grams) |
| 1,6 hexamethylene dimethacrylate with MEHQ | 3.4722 weight percent (3.618 grams) |
| Triethylene glycol dimethacrylate with MEHQ | 2.7612 weight percent (2.896 grams) |
| NN' dihydroxyethyl-p-toluidine | 0.34722 weight percent (0.3618 gram) |
| Uvinul 400 | 0.2505 weight percent (0.261 gram) |
| Titanium dioxide | 0.7466 weight percent (0.776 gram) |
| Cabosil M-5 | 0.58063 weight percent (0.605 gram) |
| MEHQ | 0.0051249 weight percent (0.00534 gram) |
| Titanium powder (untreated) | 1.0077 weight percent (1.05 grams) |
| Silanated titanium (chemically treated) | 3.0231 weight percent (3.15 grams) |

In order to prepare the catalyst component, 16.6 grams of the triethylene glycol dimethacrylate with MEHQ, 0.0254 gram of BHT and 0.5826 gram of benzoyl peroxide were added together until the BHT and benzoyl peroxide reagents were fully dissolved. Then, warm BIS-GMA (5.11 grams) was added and stirred to give a homogenous mixture. Then, aluminium oxide C (3.066 grams), 5u quartz silanized (8.18 grams) and 325M quartz silanized powder (66.43 grams) were added to the resin mixture. This resulted in approximately 100 grams of the catalyst component of the composition.

In order to prepare the base formulation, 1,6 hexamethylene dimethacrylate with MEHQ (3.618 grams), triethylene glycol dimethacrylate with MEHQ (2.898 grams), MEHQ (0.00534 gram), uvinul 400 (0.261 gram), and NN' dihydroxyethyl-p-toluidine (0.3618 gram) were all mixed together to form a homogenous solution. Titanium powder (untreated) (1.05 grams) and silanated titanium (chemically treated) (3.15 grams) were added to the solution, resulting in a black milky solution. Then, ethoxylated bisphenol A-dimethacrylate (8.69 grams) was added to produce a second homogenous solution after complete mixing. Then, warm BIS-GMA resin (13.03 grams) was added and stirred until a homogenous mixture also developed. Then, the following solids were blended together, titanium dioxide (0.776 gram), cabosil M-5 (0.605 gram), 5u quartz silanized (16.65 grams) and 325M quartz silanized (53.1 grams). This blended mixture was added to the BIS-GMA resin mixture prepared before to yield approximately 104 grams of the base formulation of the composition.

Then, equal amounts of the base and catalyst (5 grams/5 grams) components were mixed for 30 seconds. This mixing produced a setting reaction which lasted for about 3-5 minutes. As a result, a composite dental cement was formed having a compressive strength after placed for 24 hours in water of 41131 psi.

EXAMPLE 15

| Catalyst Formulation | |
| --- | --- |
| 5u quartz silanized | 8.18 weight percent (8.18 grams) |
| 325 M quartz silanized | 66.43 weight percent (66.43 grams) |
| BIS-GMA | 5.11 weight percent (5.11 grams) |
| Triethylene glycol dimethacrylate with MEHQ | 16.6 weight percent (16.6 grams) |
| Aluminium oxide C | 3.066 weight percent (3.066 grams) |
| Benzoyl peroxide | 0.5826 weight percent (0.5826 gram) |
| BHT | 0.0251 weight percent (0.0251 gram) |
| Base Formulation | |
| 325 m quartz silanized | 50.8439 weight percent (53.1 grams) |
| 5u quartz silanized | 15.9426 weight percent (16.65 grams) |
| BIS-GMA | 12.4764 weight percent (13.03 grams) |
| Ethoxylated bisphenol A-dimethacrylate | 8.3207 weight percent (8.69 grams) |
| 1,6 hexamethylene dimethacrylate with MEHQ | 3.4642 weight percent (3.618 grams) |
| Triethylene glycol dimethacrylate with MEHQ | 2.7748 weight percent (2.898 grams) |
| NN' dihydroxyethyl-p-toluidine | 0.34642 weight percent (0.3618 gram) |
| Uvinul 400 | 0.2499 weight percent (0.261 gram) |
| Titanium dioxide | 0.74494 weight percent (0.770 gram) |
| Cabosil M-5 | 0.57929 weight percent (0.605 gram) |
| MEHQ | 0.005113 weight percent (0.00534 gram) |
| Titanium powder (untreated) | 1.0053 weight percent (1.05 grams) |
| Silanated titanium (chemically treated) | 3.2459 weight percent (3.39 grams) |

In order to prepare the catalyst component, 16.6 grams of triethylene glycol dimethacrylate with MEHQ, 0.0254 gram of BHT and 0.5826 gram of benzoyl peroxide were added together until the BHT and benzoyl peroxide reagents were fully dissolved. Then, warm BIS-GMA (5.11 grams) was added and stirred to give a homogenous mixture. Then, aluminium oxide C (3.066 grams), 5u quartz silanized (8.18 grams) and 325M quartz silanized powder (66.43 grams) were added to the resin mixture. This resulted in approximately 100 grams of the catalyst component of the composition.

In order to prepare the base component, 1.6 hexamethylene dimethacrylate with MEHQ (3.618 grams), triethylene glycol dimethacrylate with MEHQ (2.898 grams), MEHQ (0.00534 gram), uvinul 400 (0.261 gram), and NN' dihydroxyethyl-p-toluidine (0.3618 gram) were all mixed together to form a homogenous solution. Titanium powder (untreated) (1.05 grams) and silanated titanium (chemically treated) (3 39 grams) were added to the solution, resulting in a black milky solution. Then, ethoxylated bisphenol A-dimethacrylate (8.69 grams) was added to produce a second homogenous solution after complete mixing. Then warm BIS-GMA resin (13.03 grams) was added and stirred until a homogenous mixture developed. Then, the following solids were blended together: titanium dioxide (0.778 gram), cabosil M-5 (0.605 gram), 5u quartz silanized (16.65 grams) and 325M quartz silanized (53.1 grams). This blended mixture was added to the BIS-GMA resin mixture prepared before to yield 104 grams of the base formulation of the composition.

Then, equal amounts of the base and catalyst (5 grams/5 grams) components were mixed for 30 seconds. This mixing produced a setting reaction which lasted for about 3-5 minutes. As a result, a composite dental cement was formed having a compressive strength after placed for 24 hours in water of 40521 psi.

Examples 2-12 represent a low viscosity composite dental cement suitable for application with dental post insertion, while Examples 13-15 represent a high viscosity dental cement suitable for application during core build-up.

In order to better appreciate the inventive composite dental cement composition, the following Table is provided to illustrate how the addition of a small amount of titanium to the composition substantially increases the compressive strength thereof.

TABLE I

| Example | Compressive Strength (psi)* (after 24 hrs in water) | SD | Value |
| --- | --- | --- | --- |
| 2 | 29534 | ±4352 | |
| 3 | 34534 | ±4281 | 0.0133 |
| 4 | 40048 | ±3021 | 0.0001 |
| 5 | 41875 | ±3273 | 0.0001 |
| 6 | 38064 | ±4086 | 0.0002 |
| 7 | 37314 | ±3413 | 0.0002 |
| 8 | 29400 | ±3390 | |
| 9 | 36332 | ±3457 | 0.0001 |
| 10 | 33400 | ±1536 | |
| 11 | 40829 | ±3676 | 0.0001 |
| 12 | 38139 | ±3187 | 0.0035 |
| 13 | 33500 | ±4541 | |
| 14 | 41131 | ±3662 | 0.0006 |
| 15 | 40521 | ±4518 | 0.0028 |

*psi = pounds/square inch

The titanium powder for the inventive composite cement was silanated (chemically modified) for incorporation chemically with the BIS-GMA (polymer) matrix. As the above Examples illustrate, using chemically modified titanium results in a chemical matrix that is stronger as compared to the BIS-GMA (see Table I).

Unmodified titanium may also be added to the cement composition, resulting in a stronger BIS-GMA matrix. However, chemically modified titanium (silanated titanium) composite cements are much stronger as compared to unmodified titanium composite cements (see Examples). Likewise, cements containing mixtures of chemical modified titanium and unmodified titanium exhibit the largest percent increases in compressive strength overall (see Table I).

Modified titanium powder interacts with the BIS-GMA (polymer) matrix, while unmodified titanium powder fills the voids located between matrixes of BIS-GMA and other acrylates, and the BIS-GMA matrix formed with the chemically modified titanium and other acrylates. Combining both the chemically modified and unmodified titanium in the cement results in the strongest BIS-GMA matrix overall and as a result the strongest composite cement.

For the above Examples, statistical analysis was performed to determine the significance between titanium based compositions and non-titanium based compositions. In each case, a two-tailed probability student's t test was considered in order to ensure complete confidence of significance (where $p<0.05$). The compressive strengths were measured after the compositions were made into cylinders (for each Example tested, a minimum of ten samples were measured) and placed into water for 24 hours. These cylinders had an average diameter of 0.185 inches and an average height of 0.450 inches. The compressive strength was calculated from the following equation: $P/r^2$, where P=pounds of force (load) and r=radius of the sample. A force was applied at a cross head speed of 0.25 inches per minute (0.635 cm/min), which resulted in samples that failed or samples that were crushed.

The composition in Example 2 had a low viscosity and is suitable to cement posts into root canals. When titanium (unmodified) is added as in Example 3, the compressive strength increases from 29534 psi to 34534 psi, a percent increase of 17% (see Table I). The p value was found to be 0.0133, which is very significant. In Example 4, silanated titanium was added and the compressive strength increased further to 40048 psi, a percent increase of 36%. Again, the p value of 0.0001 illustrated the high significance when silanated titanium is added to the composite.

The best or largest increase was found when a mixture of silanated titanium and titanium powder (not chemically treated) was added to the composition. In Example 5, with 2% silanated titanium/1% unsilanated titanium powder, the compressive strength increased to 41875 psi (a percent increase of 42%)—the composition is approaching the compressive strength of dentin. Likewise, the p value was 0.0001. This further illustrates the high significance of adding titanium to the composition.

In Examples 6 and 7, the compressive strength of the composition increased from 29534 psi (for the composition in Example 2) to 38064 psi in Example 6 (2% silanated titanium/0.5% titanium powder/0 5% $YbF_3$ (ytterbium fluoride)) and 37314 psi in Example 7 (2% silanated titanium/1.0% titanium powder/1.0% $YbF_3$ (ytterbium fluoride)). This represents a percent increase of 29% for Example 6 and 26% increase for Example 7, with a p value of 0.0002 for Examples 6 and 7.

Next, sodium fluoride (NaF) was added along with the chemically modified titanium and titanium powder. In particular, Example 8 was the composition of Example 2 with 0.625% of NaF added. The compressive strength was measured to be 29400 psi. When a mixture of silanated titanium and titanium powder is added as in Example 9, the compressive strength increased to 36332 psi (an increase of 24%) with a p value of 0.0001. In Example 10, the amount of NaF is raised to 1% and the compressive strength was measured to be 33400 psi. In Example 11, a mixture of silanated titanium with unsilanated titanium was added and the compressive strength increased to 40829 psi (a percent increase of 14%). In Example 12, chemically treated titanium powder was added only and the compressive strength increased to 38139 psi (an increase of 22%). The p values for these two Examples were 0.0001 for Examples 11 and 0.0035 for Example 12. Example 13 represents a core paste composition having a high viscosity and a compressive strength of 33500 psi. Again, when a mixture of silanated titanium and unsilinated titanium was added to the core paste composition, the compressive strength was raised to 41131 psi (Example 14) and 40521 psi (Example 15). This represents a percent increase of 23% for Example 14 and 21% for Example 15 with a p value of 0.0006 and 0.0028 respectfully.

The above Examples (2–15) illustrate the effectiveness of the inventive composition, particularly the increase in compressive strength when small amounts of titanium (modified)/titanium (unmodified) are added to the polymer matrix.

Application of the inventive dental cement composition is as follows. Initially, the dentist or other dental personnel prepares a post-hole in the selected tooth. Post-hole preparation begins with the removal of root filling material using a reaming device. Then, a cutting drill is used to substantially create the hole—using the cutting drill, 100% of the post-hole length and 90% of the post-hole width are created. Then, a primary reamer is used to establish the entire width of the hole to make sure that it is substantially concentric.

After preparing the post-hole, the dentist selects the desired dental post, which is first temporarily inserted into the hole for trial purposes. If the dental post appears to be acceptable, the dentist will then first place a low viscosity composite dental cement composition made in accordance with the invention in the post-hole and on the post itself. Then, the post is inserted into the post-hole and threaded with light pressure. The post should seat completely with minimal resistance. After seating is completed, excess cement is removed.

In order to complete the process, it is necessary to form a core over the tooth and inserted post. This process is known as "core build up" and is carried out using a high viscosity composite dental cement composition made in accordance with the invention. The cement composition is placed in the core form and seated over the post using moderate pressure to ensure close adaptation of the composite cement to the core.

It will thus be seen that the objects set forth above, among those made apparent from the proceeding description, are efficiently attained, and since certain changes made by made in carrying out the above method and in preparing the composition as set forth above without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A composite dental cement composition comprising:
    a polymer matrix in an amount between about 10 and 50 weight percent;
    a filler in an amount between about 35 and 80 weight percent; and titanium powder in an amount between about 2 and 5 weight percent, wherein the titanium powder includes silinated titanium powder comprising at least 2% by weight of the cement composition.

2. The composition of claim 1, wherein the polymer matrix comprises an epoxy matrix.

3. The composition of claim 2, wherein the epoxy matrix comprises an acrylic matrix.

4. The composition of claim 3, wherein the acrylic matrix is formed from monomers of methacrylate.

5. The composition of claim 4, wherein the monomers of methacrylate are selected from the group of monomers of dimethacrylate including bisphenol A-glycidyl methacrylate, triethylene glycol dimethacrylate, tetraethylene glycol dimethacrylate, ethylene glycol dimethacrylate, diethyleneglycol dimethacrylate, butanediol dimethacrylate, isobisphenol A-glycidyl methacrylate, trimethylolpropane dimethacrylate, hexanediolethylene dimethacrylate, neopentyl glycol dimethacrylate, bisphenol A-ethoxylated dimethacrylate and bisphenol A-dimethacrylate.

6. The composition of claim 5, wherein the monomer of dimethacrylate is bisphenol A-glycidyl methacrylate in an amount between about 5 and 50 weight percent based on the total weight of the cement.

7. The composition of claim 1, wherein the filler is selected from the group including quartz, silicon dioxide, fumed silicon dioxide, aluminum dioxide, titanium dioxide, zirconium dioxide, silicas, glass, graphite fibers, boron fibers, barium glass, alumina silicates, boro silicate glass, glass powders, hydroxy apatite, wood, micas and asbestos.

8. The composition of claim 1, wherein at least some of the titanium is not chemically treated.

9. The composition of claim 1, wherein the silanated titanium powder is prepared from a silane selected from the group including gamma-methacryloxy propyltrimethoxysilane, gamma-methacryloxy propyl-tris-(2-methoxyethyoxy) silane, vinyl trichlorosilane, vinyl triethyoxysilane, vinyl trimethoxysilane and vinyl triacetoxysilane.

10. The composition of claim 1, wherein the titanium powder has a particle size of between about 1 and 30 microns.

11. The composition of claim 3, wherein the titanium powder has a purity of at least a 98%.

12. The composition of claim 1, further including a fluoride in an amount between about 0.5 and 6 weight percent.

13. The composition of claim 12, wherein the fluoride is selected from the group including sodium fluoride, tin fluoride, ytterbium fluoride, an amine fluoride and an acidulated phosphate fluoride.

14. A system for preparing a composite dental cement composition comprising:
a catalyst component including a catalyst in an amount between about 0.2 and 2.0 weight percent, at least one epoxy monomer in an amount between about 15 and 50 weight percent and a filler in an amount between about 40 and 80 weight percent;
a base component comprising a base in an amount between about 0.2 and 1.5 weight percent, at least one epoxy monomer in an amount between about 20 and 50 weight percent and a filler in an amount between about 45 and 85 weight percent; and
titanium powder in an amount between about 2 and 5 weight percent based on the combined amount of catalyst, base and titanium powder;
wherein the titanium powder includes silinated titanium powder comprising at least 2% by weight of the combined amount of catalyst, base and titanium powder;
wherein the catalyst component, base component and titanium powder are combined in order to form the composite dental cement composition.

15. The system of claim 14, wherein the catalyst of the catalyst component comprises a free radical source.

16. The system of claim 15, wherein the free radical source comprises an organic peroxide.

17. The system of claim 16, wherein the organic peroxide is selected from the group including benzoyl peroxide, acetyl peroxide, parachlorobenzoyl peroxide, cumyl peroxide, t-butyl peroxide, lauroyl peroxide, t-butyl hydroperoxide, methylethyl ketone peroxides, t-butyl peroxy-benzoate, 2,5 dimethylhexane-2,5 dihydroxy peroxide and t-cumyl hydroperoxide.

18. The system of claim 17, wherein the organic peroxide is benzoyl peroxide.

19. The system of claim 14, wherein said at least one epoxy monomer comprises at least one monomer of methacrylate.

20. The system of claim 18, wherein the at least one monomer of methacrylate is bisphenol A-glycidyl methacrylate.

21. The system of claim 14, wherein the base comprises an amine compound.

22. The system of claim 21, wherein the amine compound is selected from the group including toludine compounds, propylamine, butyl N-butyl amine, pentylaamine, hexylamine, dimethylamine, diethyleneamine, dipropylamine, di-n-butylamine, dipentylamine, trimethylamine, triethylamine, tripropylamine, tri-n-butyl amine, trimethyl amine, long chain fatty amine, tri-n-butylamine, tripentylamine, 4-methylaniline, N-N-bis-(2-hydroxyethyl)-3,5-dimethylaniline, N-methyl-N(2-hydroxyethyl)-4-methylaniline, long chain fatty amines, diamine, trimethylene diamine, tetramethylene diamine, pentamethylene diamine and hexamethylene diamine.

23. The system of claim 22, wherein the amine compound comprises a toluidine compound.

24. The system of claim 23, wherein said toluidine compound comprises NN' dihydroxyethyl toluidine.

25. The system of claim 14, wherein the silanated titanium powder is prepared from a silane selected from the group including gamma-methacryloxy propyltrimethoxysilane, gamma-methacryloxy propyl-tris-(2-methoxyethyoxy) silane, vinyl trichlorosilane, vinyl triethyoxysilane, vinyl trimethoxysilane and vinyl triacetoxysilane.

26. The system of claim 14, wherein the titanium powder has a particle size of between about 1 and 30 microns.

27. The system of claim 26, wherein the titanium powder has a purity of at least 98%.

28. The system of claim 14, wherein the titanium powder is added to the catalyst component prior to combining the catalyst component with the base component.

29. The system of claim 14, wherein the titanium powder is added to the base component prior to combining the catalyst component with the base component.

30. A composite dental cement composition comprising:
a polymer matrix in an amount between about 15 and 50 weight percent;
a filler in an amount between about 35 and 80 weight percent; and
titanium powder that has been chemically treated by silination in an amount between about 2 and 5 weight percent.

* * * * *